US005408891A

United States Patent [19]
Barber et al.

[11] Patent Number: 5,408,891
[45] Date of Patent: Apr. 25, 1995

[54] FLUID PROBE WASHING APPARATUS AND METHOD

[75] Inventors: Duane G. Barber, Yorba Linda; David E. Dalke, La Habra, both of Calif.

[73] Assignee: Beckman Instruments, Inc., Fullerton, Calif.

[21] Appl. No.: 991,785

[22] Filed: Dec. 17, 1992

[51] Int. Cl.⁶ .......................... G01N 35/00; G01N 1/14
[52] U.S. Cl. ................................ 73/864.22; 73/864.34
[58] Field of Search ............. 73/864.34, 864.35, 864.22, 73/864.25, 864.24, 864.73, 864.74; 422/81; 436/50, 51, 54, 180

[56] References Cited

U.S. PATENT DOCUMENTS

| | | | |
|---|---|---|---|
| 3,266,322 | 8/1966 | Negersmith et al. | 73/864.22 |
| 3,719,086 | 3/1973 | Bannister . | |
| 3,748,911 | 7/1973 | Rousselet et al. | 73/864.22 |
| 3,826,621 | 7/1974 | Johnson, Jr. et al. . | |
| 3,842,680 | 10/1974 | Vollick et al. . | |
| 3,912,456 | 10/1975 | Young | 73/864.22 X |
| 3,960,020 | 6/1976 | Gordon et al. | 73/864.22 |
| 4,058,252 | 11/1977 | Williams | 141/130 X |
| 4,108,608 | 8/1978 | Maher, Jr. et al. | 222/137 X |
| 4,302,421 | 11/1981 | Baker | 422/64 |
| 4,318,885 | 3/1982 | Suzuki et al. | 422/63 X |
| 4,323,537 | 4/1982 | Mody | 422/63 |
| 4,434,672 | 3/1984 | Williams et al. | 73/864.22 |
| 4,456,037 | 6/1984 | Gocho | 141/1 |
| 4,495,149 | 1/1985 | Iwata et al. | 422/65 |
| 4,516,437 | 5/1985 | Pedroso et al. | 73/864.22 |
| 4,543,238 | 9/1985 | Mimura et al. | 422/63 |
| 4,590,165 | 5/1986 | Gilles et al. | 436/49 |
| 4,799,393 | 1/1989 | Uffenheimer | 73/864.22 |
| 4,817,443 | 4/1989 | Champseix et al. | 73/864.22 |
| 4,820,497 | 4/1989 | Howell | 422/63 |
| 4,835,110 | 5/1989 | Seymour et al. | 436/517 |
| 4,871,682 | 10/1989 | Mazza | 436/179 |
| 4,888,998 | 12/1989 | Buzza et al. | 73/864.21 |
| 4,891,104 | 1/1990 | Liston et al. | 204/403 X |
| 4,908,320 | 3/1990 | Zakowski et al. | 436/45 |
| 4,935,106 | 6/1990 | Liston et al. | 204/153.1 |
| 4,948,563 | 8/1990 | Kanewske, III | 422/99 |
| 4,965,049 | 10/1990 | Lillig | 422/68.1 |
| 5,055,408 | 10/1991 | Higo et al. | 436/48 |
| 5,066,336 | 11/1991 | Hoffman et al. | 134/22.12 |
| 5,079,959 | 1/1992 | Miyake et al. | 73/864.22 X |
| 5,132,233 | 7/1992 | Jackson et al. | 430/179 |
| 5,133,373 | 7/1992 | Hoffman et al. | 73/864.22 X |

FOREIGN PATENT DOCUMENTS

| | | | |
|---|---|---|---|
| 2538451 | 3/1976 | Germany | 73/864.22 |
| 2547843 | 4/1977 | Germany | 73/864.22 |
| 2075672 | 11/1981 | United Kingdom | 73/864.22 |

*Primary Examiner*—Tom Noland
*Attorney, Agent, or Firm*—William H. May; Arnold Grant; Merchant & Gould

[57] ABSTRACT

A probe washing apparatus including a probe having a tip and a wash collar having a bore coaxially aligned with the probe, the wash collar including ports for applying a vacuum and a wash liquid to the wash collar bore. The probe may be displaced vertically with respect to the wash collar to aspirate and dispense liquids, and the wash collar and probe are displaced together laterally. The steps of washing the probe tip include raising the probe to a position with the probe tip within the bore, applying vacuum to the bore, flushing the interior of the probe, and flushing the exterior of the probe.

19 Claims, 3 Drawing Sheets

FLUID PROBE WASHING APPARATUS AND METHOD

FIELD

The present invention is related to the field of fluid probe handling devices and systems and more particularly to apparatus and methods for washing fluid handling probes. Although not to be limited to this particular use, the present invention is useful in the field of automated clinical chemistry analyzers.

BACKGROUND

Automated clinical chemistry analyzers are well known in the art and are generally used for the automated or semi-automated analysis of patient samples. Typically, prepared patient samples, such as blood, urine, spinal fluid and the like, are placed onto such an analyzer in sample containers such as test tubes. The analyzer pipettes a patient sample and one or more reagents to a reaction cell or cuvette where a chemical analysis of the sample is conducted, usually for a particular analyte of interest, and the results of the analysis are reported.

Automated pipettors are employed on such analyzers to transfer the patient samples and reagents as required for the specified analysis. Such pipettors can include a hollow probe having an open end or tip. The probe is, for example, lowered into a sample container that holds a sample, a predetermined volume of sample is withdrawn from the sample container, and the probe is withdrawn from the sample container. The probe is moved, for example, to a position above a reaction cell, is again lowered, and the sample held in the probe is expelled into the reaction cell. Similar actions may be used to pipette and deliver one or more reagents from reagent containers to the reaction cell, either with the same probe or with one or more reagent delivery probes.

To prepare such a probe for a subsequent delivery, the probe is washed to eliminate as much as possible any residue from the prior samples or reagents that were handled by the probe. Probe washing may be accomplished by, for example, lowering the probe tip into a wash cell that contains a wash fluid such as water. The wash fluid washes the exterior of the probe tip, and the interior of the probe may be cleaned by aspirating and discharging the wash fluid or, alternatively, discharging a wash fluid through the probe into the wash cell.

A common problem with probe washing, however, is carryover, that is, the residual fluid or contaminates from a fluid that remain on or in or may be absorbed by the probe despite washing. This residue mixes with subsequent sample or reagents drawn into the probe and can interfere with subsequent analyses.

Another problem with probe washing is the time needed to move the probe to a wash station and accomplish the probe washing. Substantial time can be required to wash the probe. For example, if the probe has delivered a sample to a reaction cell, the probe must be raised, moved to a position over a wash cell, and lowered into the cell for washing. Once washing is done, the probe must again be raised and moved on to the next operation.

Still another drawback of prior systems is washing a probe that has been inadvertently inserted into, for example, a sample or reagent to a depth that conventional washing cups and cells can not clean. Probes often include or are provided externally with some form of liquid level detection. This allows the probe to be inserted until the tip touches the surface of the liquid, where liquid contact is sensed. The probe may then be lowered an additional distance sufficient for the volume of liquid to be drawn into the probe or may be lowered as liquid is drawn into the probe. In either instance, only a relatively short, predetermined portion of the outside of the probe tip is contaminated with the liquid. Thus, the probe tip can be cleaned in a conventional wash cell or cup that is required to clean only a short portion of the probe tip, reducing cleaning time and the volume of washing liquid required.

If the liquid level sensing used to detect the contact of the probe tip with the surface of the liquid should fail, however, the probe will be lowered some predetermined distance that may represent the maximum insertion distance permitted to avoid the probe tip striking the bottom of the liquid reservoir. If the vessel actually is full or substantially full of liquid, the entire length of the submerged probe exterior becomes contaminated with the liquid. This length may well exceed the probe length that can be accommodated by the washing cell or cup, requiring operator intervention to manually clean the probe and return the probe, and the automated analyzer in which the probe is used, to service.

Thus, there is a need for a probe washing apparatus and method of use of such an apparatus that overcomes these limitations of the prior art probe washing approaches, including but not limited to reduced carryover, decreased probe washing time, and variable exterior probe tip lengths that may be coated with contaminating liquids.

SUMMARY OF THE INVENTION

An apparatus in accordance with the present invention overcomes such limitations and drawbacks and includes a hollow probe having a tip and a wash collar that is aligned coaxially with the probe. The wash collar includes a bore through which the probe is received, the bore being open at both ends thereof about the probe. The apparatus further includes vacuum means for applying a vacuum to the bore, bore pumping means for pumping a wash fluid through the wash collar bore, and probe pumping means for pumping a wash fluid through the probe and out of the probe tip.

The bore of the wash collar may further include an upper portion having a first diameter larger than the outside diameter of the probe and a central chamber portion having a diameter larger than the upper portion and including a port in fluid communication with the vacuum means.

A lower portion of the wash collar bore may include a portion having a tapered cross section, tapering from a larger diameter to a smaller diameter and proximate the central chamber portion.

The bore may further include a reduced portion between the lower portion and the central chamber having a diameter less than the largest diameter of the chamber portion, and selected such that liquid carried by the exterior of the probe wicks to the reduced portion as the probe is drawn through the wash collar.

The lower portion of the wash collar bore may include a port in fluid communication with the bore pumping means. The reduced portion is above the lower portion and the port such that the reduced portion itself may be washed by the flow of wash liquid from the bore pumping means upwardly past the reduced portion and into the central chamber and out of the wash collar by way of the vacuum means.

A method for using the wash collar of the present invention includes activating the vacuum means to apply a vacuum to the bore, activating the probe pumping means to pump wash fluid through the probe and out of the probe tip, deactivating the probe pumping means, activating the bore pumping means for pumping wash fluid through the wash collar bore and around the exterior of the probe tip, deactivating the bore pumping means, and deactivating the vacuum means. Preferably, the steps are performed sequentially.

The method may further include an initial step of positioning the probe tip within the wash collar bore.

The step of deactivating the probe pumping means may occur before the step of activating the bore pumping means. The step of deactivating the probe pumping means may occur after the step of activating the bore pumping means. The steps of activating and deactivating the probe pumping means may be timed to create a flow of wash fluid through the probe tip for between about one and two seconds. The steps of activating and deactivating the bore pumping means may be timed to create a flow of wash fluid around the outside of the probe tip for less than about one second.

Advantageously, the probe and probe wash collar are preferably carried together and the coaxial alignment between the two is maintained by way of, for example, an arm or other suitable support, with the arm including means for displacing the arm and the probe and probe wash collar laterally. The lateral displacement may be about a central pivot point or may be linearally moveable or a combination of pivotable and linearally moveable. Thus, washing of the probe may be accomplished as the probe moves from one station to another, decreasing wash time and increasing system throughput.

Further, the wash collar and associated vacuum and pump means may be activated as the probe is drawn up into the wash collar, enabling the entire active length of the probe, that is, the entire external length of the probe that may be exposed to contaminating liquids, to be cleaned as the probe is withdrawn.

Thus, the apparatus and method of the present invention reduces carryover by thoroughly washing the exterior and interior of the probe, decreases wash time my providing the probe washing "on the fly" as the probe moves from operation station to operation station, and cleans the entire active length of the probe exterior to overcome inadvertent contamination of the external surface of the probe if a liquid level sensing or related control apparatus should fail.

BRIEF DESCRIPTION OF THE DRAWINGS

These and other advantages of the present invention will be apparent from the following drawings in which.

DETAILED DESCRIPTION

Figure 1:
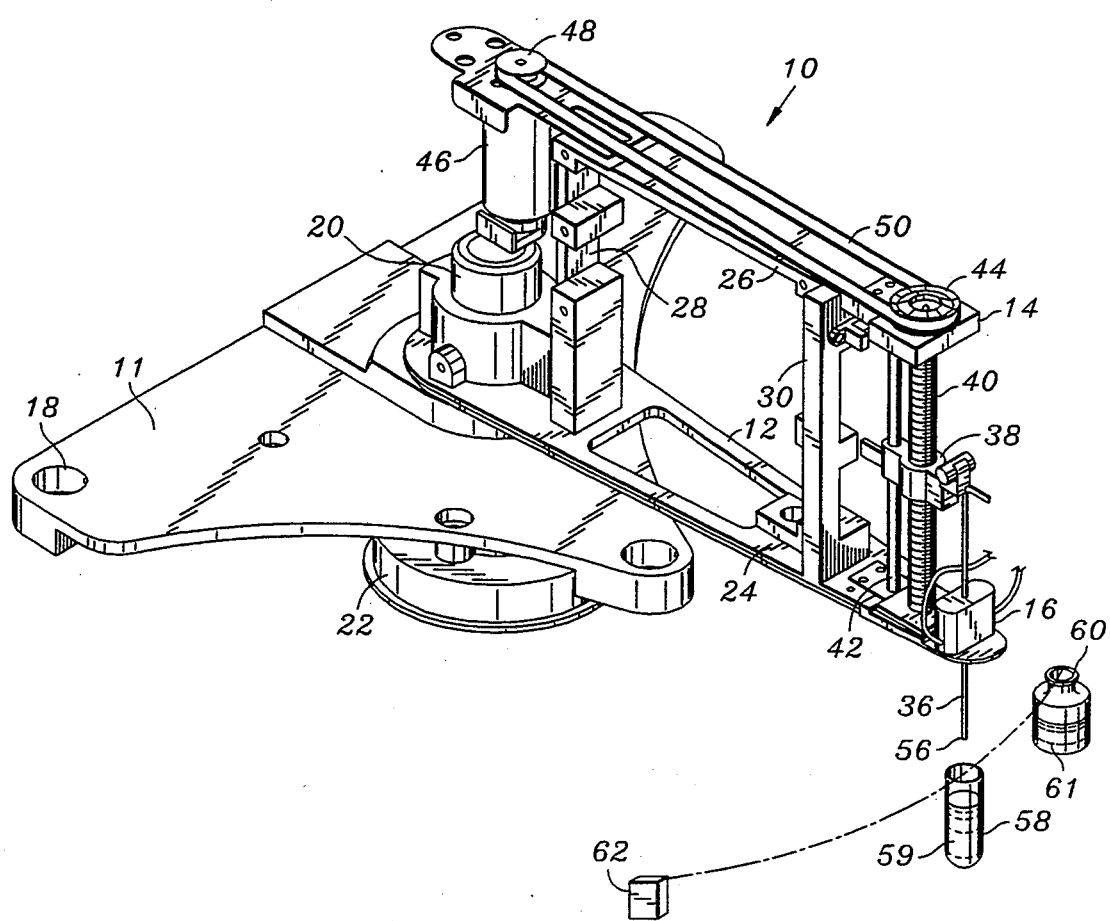
FIG. 1 is a simplified perspective view of the apparatus of the present invention.

With reference to FIG. 1, a probe washing apparatus 10 in accordance with the present invention and that is adapted to perform the method of the present invention includes base plate 11 and a pivotable arm 12, the pivotable arm 12 supporting a probe assembly 14 and a wash collar 16. The base plate 11 includes suitable mounting holes 18 and a rotatable shaft 20 that may be rotated by means of a pulley 22. The pulley 22 may in turn be driven through a drive belt (not shown) by a motor (not shown).

The arm 12 is removably fixed at a first or pivot end of the arm 12 to the shaft 20 and carries the probe assembly 14 at a second or outer end of the arm 12. The arm 12 includes bottom and top horizontal members 24, 26, respectively, and first and second vertical members 28, 30, respectively.

The probe assembly 14 is disposed at the outer end of the arm 12. The probe assembly 14 includes a hollow, fluid-carrying probe 36 that is fixed at its upper end to a moveable block 38. The block is in turn threaded to a threaded vertical shaft 40 and a guide bar 42 on the opposite side of the shaft 40 from the probe 36. The threaded shaft 40 is journaled at its upper and lower ends for rotation and is fixed to a pulley 44 above the top horizontal member 26. The threaded shaft 40 may be rotated by means of a motor 46 disposed at the pivot end of the arm 12, the motor operatively connected by means of a pulley 48 and a flexible belt 50 to the pulley 44.

The wash collar 16 is fixed to the bottom horizontal member 24 at the outer end of the arm 12 and is aligned with and receives the probe 36. The probe 36 passes freely through the wash collar 16. A lower open tip 56 of the probe may be aligned (as is described below with respect to the operation of the apparatus 10 and the method of the present invention), for example above a test tube 58 that may contain a sample 59 to be tested, a reagent container 60 from which reagent 61 may be withdrawn, and a reaction cuvette 62 into which sample 59 and reagent 61 may be expelled for reaction and measurement. The test tube 58, reagent container 60 and reaction cuvette 62 may all be of conventional design and may be on, for example, wheels, belts, or may be stationary, depending on the particular design of an analyzer in which the apparatus 10 of the present invention may be used.

Figure 2:
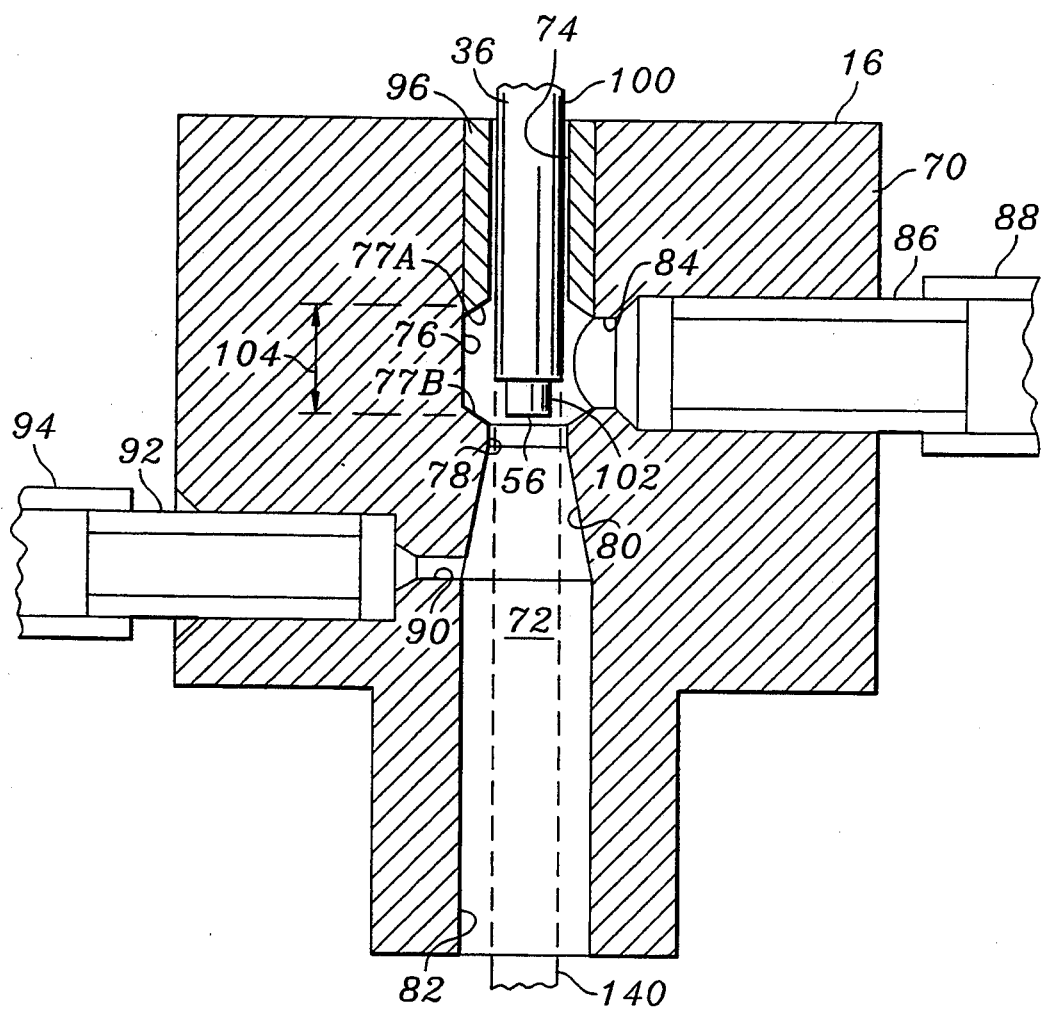
FIG. 2 is a cross section view of the wash collar included in the apparatus of FIG. 1.

With reference to FIG. 2, the wash collar 16 is illustrated with the probe 36 in a retracted or "up" position. The wash collar 16 includes a body 70 formed from, for example, PEEK (polyether-ether-ketone). A bore 72 is formed vertically through the wash collar 16, the bore including an upper portion 74, a washing or central chamber 76, a restricted or reduced portion 78, a tapered portion 80, and a lower portion 82, respectively, top to bottom, as seem in FIG. 2. The upper portion 74 has cylindrical side walls and has an inside diameter slightly larger than the outer diameter of the probe 36. The central chamber 76 is enlarged with respect to the upper portion 74. The central chamber 76 includes upper and lower tapered walls 77A and 77B, respectively. A port 84 is formed into the side wall of the chamber 76 between the upper and lower tapered walls 77A and 77B and is connected by a suitable fitting 86 to a length of tubing 88 which is in turn connected to a controllable vacuum source as described with reference to FIG. 3 below.

Immediately below the chamber 76 is the reduced portion 78 which has the same diameter as the upper portion 74. The tapered portion 80 tapers outwardly from the diameter of the reduced portion 78 to the lower portion 82, the lower portion having a diameter approximately the same or slightly less than the diameter of the chamber 76. A wash liquid port 90 is formed through the wall of the wash collar 16, intersecting the bore 72 immediately above (as seen with respect to FIG. 2) the intersection of the tapered portion 80 and lower portion 82. The port 90 is connected by a fitting 92 to a length of tubing 94 which is in turn connected to a source of wash liquid as described with reference to FIG. 3 below.

The upper portion 74, central chamber 76, reduced portion 78, tapered portion 80 and lower portion 82 are all coaxial and all but the tapered portion have cylindrical side walls. The bore 72 throughout its length is sized to freely receive the probe 36 and provide annular spaces or gaps between the portions of the bore 72 and the exterior surface of the probe 36 that may be received within the bore 72. The bore 72 and ports 84, 90 may be formed by, for example, drilling. An insert 96 may be fixed within the body 70 to define the upper portion 74 and the upper tapered wall 77A of the central chamber 76.

As seen with reference to FIG. 2, the probe 36 includes an outer shell 100 and an inner fluid carrying conduit 102. The shell 100 and conduit 102 and both preferably metal and are separated by an insulating compound (not shown). The outer shell 100 and inner fluid carrying conduit 102 are electrically connected to a liquid level detection device (not shown) which may detect the contact of the probe tip 56 with the surface of a liquid by sensing, for example, increased conductivity between the shell 100 and conduit 102. Such a liquid level detection device may be of conventional design and is well known in the art.

Figure 3:
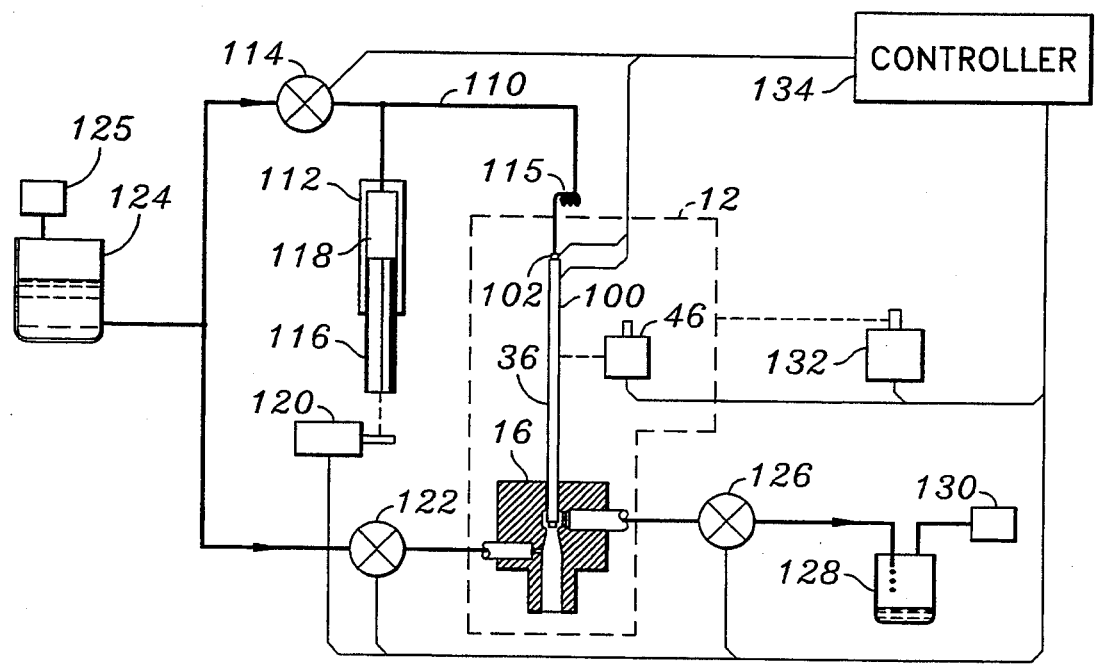
FIG. 3 is a schematic diagram of the apparatus of the present invention as connected to a fluid system and control system.

The apparatus of the present invention may be integrated into and controlled by the fluid and control system of FIG. 3. The inner liquid carrying conduit 102 of the probe 36 is connected via tubing 110 to an automated syringe 112 and a solenoid controlled valve 114. Preferably, the tubing 110 is formed into a coil 115 proximate the top of the probe 36, the coil providing turbulence as liquid flows through the probe 36 to thus generate a mixing action in such liquid flow. The automated syringe 112 is conventional in design and includes a piston 116 operable in a chamber 118, the piston 116 being connected to and operated by a motor 120. The valve 114 controls the flow of a wash liquid from a pressurized wash liquid reservoir 124. The tubing 94 from the wash liquid port 90 in the wash collar 16 is connected to a solenoid controlled valve 122 which controls the flow of a wash liquid from the reservoir 124. The reservoir may be pressurized by way of a regulated air pump 125. The tubing 88 connected to the vacuum port 84 in the wash collar 16 is connected via a solenoid controlled valve 126 to a waste reservoir 128 to which is applied a regulated vacuum from a vacuum pump 130.

As described above with respect to FIG. 1, the motor 46 is actuated to displace the probe 36 vertically, either up or down, and a motor 132 pivots the arm 12 via the shaft 20. The valve 114, motor 120, valve 122, valve 126, motor 46 and motor 132 are all controlled by a controller 134 which may be of conventional design and which is programmed to control the operation of the system in accordance with the method of the present invention. The outer shell 100 and inner fluid carrying conduit 102 are electrically connected to the controller which includes level sensing circuitry such as that described above.

In operation, the initial condition of the apparatus 10 is with the probe 36 in the retracted or up position as shown in FIG. 2. In such a position, a probe tip length 104 is within the central chamber 76. The initial condition of the apparatus also preferably includes the arm 12 positioned with the probe aligned vertically over, for example, the test tube 58 which contains a volume of liquid sample 59. The motor 46 is operated to lower the probe 36 toward the sample 59. When the tip 56 of the probe 36 contacts the surface of the sample 59 and the level sensing circuitry within the controller 134 senses the surface of the sample 59, the motor 46 is turned off and motor 120 is energized to draw sample 59 into the probe 36 through the tip 56. The probe 36 is inserted into the sample 59 a distance that is less than the length 104 of the probe 36 within the central chamber 76 when the probe 36 is in its retracted or up position. This can be accomplished, for example, if the volume of sample drawn into the probe 36 lowers the sample level within the test tube 58 less than such distance. Alternatively, if more sample is required, the motor 46 may be controlled to lower the probe 36 slightly as the sample is aspirated into the probe 36, essentially following the level of the sample 59 down.

When a predetermined volume of sample has been aspirated, the motor 120 is turned off and motor 46 is operated to raise the probe 36 to the up or retracted position with the tip 56 positioned as shown in FIG. 2 within the wash collar 16. The motor 132 is activated to reposition the arm 12 and probe 36 with the probe 36 aligned, for example, above the cuvette 62. The motor 132 is turned off and motor 46 is controlled to lower the probe 36 to a position with the tip 56 above the cuvette 62, and the motor 120 is controlled to expel the sample within the probe 36 into the cuvette 62. When the sample has been expelled, the motor 120 is turned off and the motor 46 is controlled to raise the probe 36 into its retracted position. The motor 132 is again controlled to pivot the arm 12 toward, for example, the reagent container 60.

As the arm 12 is moving toward the reagent container, the probe is washed within the wash collar. More particularly, the vacuum valve 126 is energized to draw air into the wash collar 16 through the lower portion 82 and, to a substantially lesser extent, through the small annular space between the probe 36 and the upper portion 74. The valve 114 is energized to flow pressurized wash liquid through the probe 36 and discharge the wash liquid through the probe tip 56, washing the inside of the probe 36 and swirling the expelled wash liquid about the exterior of the probe tip 56 and the length 104 of the probe 36 within the central chamber 76. The wash liquid is drawn out of the central chamber by the air flow created by the vacuum applied to the vacuum port 84.

After a length of time of between about one and two seconds, and preferably about 1.4 seconds in the embodiment disclosed herein, the valve 114 is closed and the external wash fluid valve 122 is opened to flow wash liquid into the tapered portion 80. This wash liquid is drawn upwardly through the tapered portion 80, past the reduced portion 78 and into the central chamber, drawing the wash liquid and around the tip of the probe 36 and the length 104 of the probe 36 within the central chamber 76, washing the exterior of the probe of any contaminates remaining after the internal wash is completed.

The valve 122 is held open to supply wash liquid through the wash liquid port 90 for about one second, and preferably in the embodiment disclosed herein, for about 0.6 second. The vacuum valve 126 is closed about one to two seconds after the last wash liquid is flowed into the central chamber 76, and preferably in the disclosed embodiment, about 1.5 seconds.

The internal probe wash and external probe wash accomplished by the opening and closing of valves 114 and 122 may also be accomplished such that an overlap of the washing liquid flow times occurs. Thus, instead of the valve 114 closing before the valve 122 is opened, the valve 122 may first be opened to initiate the flow of external wash liquid and then the internal wash liquid valve 114 may then be closed. In either case, that is, where there is no overlap in time of the internal wash flow from valve 114 and then from valve 122, or where there is such an overlap in time, the external wash valve 122 preferably closes last, allowing external wash liquid to flow around the outside length 104 of the probe 36 within the central chamber 76 to thus finish the external cleaning of the probe 36.

It is to be understood that this probe cleaning cycle may be performed while the arm 12 is moving from a position over the cuvette 62 to a position with the probe 36 over the reagent container 60, thus allowing for probe cleaning "on the fly" rather than interrupting the arm 12 movement to wash the probe 36 at a separate wash station as would otherwise be required in a prior art system. The wash sequence in the embodiment disclosed herein lasts approximately 2.3 seconds overall.

The probe washing cycle just described may also be performed before the probe 36 is used, for example, to pick up sample 59 or reagent 61, if the probe 36 has been idle for more than about fifteen seconds. Such a cleaning allows liquid carried within the probe that may leach contaminates out or off of the internal surface of the fluid carrying conduit 102 to be washed out of the probe 36, further reducing carryover and contamination between uses of the probe 36.

Another aspect of the method of the present invention is a washing cycle that may be conducted to clean the probe 36 if the liquid level sensing fails. In such an instance, the probe may be inserted into sample or reagent to a depth that exceeds the length 104 of the probe that is within the central chamber 76 during the normal cleaning cycle described above.

For example, the liquid level sensing may fail when the probe 36 is lowered into the reagent container 60. With no reagent 61 level feedback to the controller 134, the probe 36 is inserted into the reagent container 60 to a predetermined distance, for example, representing the maximum insertion depth allowed without running the probe tip 56 into the bottom of the reagent container 60. However, this allows the probe 36 to be coated, or potentially coated, a distance up the exterior of the probe greater than normal cycle cleaning length 104.

If the controller 134 detects such a condition, that is, no liquid level is detected before the probe 36 is fully inserted into the reagent container 60, the controller conducts a level sense failure (i.e., extended probe exterior length) cleaning procedure. In such a procedure, the vacuum valve 126 is opened and the external wash valve 122 is opened, flowing wash liquid into the collar 16 and around the exterior of the probe 36 as the probe 36 extends through the wash collar 16 as shown by the phantom lines 140 of the probe exterior in FIG. 2. The motor 46 is controlled to raise the probe up at, for example, about one inch per-second, washing the probe 36 exterior as it is raised to the retracted position with the tip 56 within the central chamber 76. The internal wash valve 114 is energized to turn on the wash liquid through the interior of the probe 36. The internal wash lasts less than a second in the embodiment disclosed herein and more particularly may last about 0.5 second, the interior wash valve 114 is closing to end the internal wash after the internal wash time interval. The exterior wash valve 122 is closed less than one second later (in the preferred embodiment disclosed here, about 0.4 second later) and the vacuum valve 126 is closed less than two seconds after the external wash valve 122 closes. In the embodiment disclosed herein, the delay to the closing of the vacuum valve 126 is about 1.5 seconds.

In accordance with one aspect of the method of operation of the present invention, the probe may be washed after aspiration of a liquid, such as the sample 59 or reagent 61, but before the liquid is delivered via the probe 36 to, for example, the reaction cuvette 62. If a predetermined volume of sample 59 is drawn into the probe 36 as described above, the probe 36 is raised to the retracted position with the probe tip length 104 within the central chamber 76. The motor 120 is operated to withdraw the aspirated sample into the probe 36, leaving an air slug between the end of the aspirated sample within the probe 36 and the open end 56. The vacuum valve 126 is opened and then the external wash valve 122 is opened, providing an external wash of the probe tip length 104. The external wash valve 122 is closed and the vacuum valve 126 is closed, preferably in that order, to end the external probe tip wash, and the probe 36 is then ready to dispense the aspirated sample.

The present invention provides significant flexibility to the designers of analytical instruments in that the probe tip can be washed any time the probe tip length 104 is within the central chamber 76. The probe tip washing can occur as the arm 12 is moving to position the probe 36 for use rather than moving the probe 36 to a specific wash station location as is conventional in the prior art.

It is to be appreciated that although the embodiment disclosed includes arm 12 that swings the probe 36 in an arc above, for example, the reaction cuvette 62, test tube 58 and reagent container 60, the probe 36 and wash collar 16 may be carried by other forms of displacement mechanisms, such as those that carry the probe 36 and wash collar 16 along a linear, curvilinear or other straight or curved paths.

The present invention is not to be limited to the particular embodiment disclosed herein but is to be defined and interpreted only according to the full scope of the appended claims hereto and all equivalents thereof.

We claim:
1. A probe washing apparatus, comprising:
 a hollow probe having a tip and an exterior surface;
 displacement means for moving the probe vertically;
 a wash collar, the wash collar including a bore through the wash collar adapted to receive the probe, the bore being sized to define a gap between an outside dimension of the probe and an inside dimension of the bore, the wash collar bore including an upper portion having a first diameter larger than an outside diameter of the probe and a central chamber portion having a diameter larger than the first diameter of the upper portion and including a port in fluid communication with a vacuum means, and the wash collar bore further including a lower portion having a cross section extending from a larger diameter to a smaller diameter proximate the central chamber portion, and further including a reduced portion between the lower portion and the central chamber having a diameter less than a largest diameter of the chamber portion, the diameter of the reduced portion being sized to be spaced from the probe to facilitate wicking liquid from the exterior surface of the probe;

means for fixing the wash collar laterally and vertically with respect to the probe, the bore being coaxially aligned with the probe for vertical displacement of the probe through the bore;

vacuum means for applying a vacuum to the bore to draw liquid out of the bore;

bore pumping means for pumping a wash liquid through the wash collar bore; and probe pumping means for pumping a wash liquid through the probe and out of the probe tip.

2. An apparatus as in claim 1 wherein the lower portion includes a port in fluid communication with the bore pumping means.

3. A method for using the apparatus of claim 1 including the steps of:

positioning the probe tip within the coaxially aligned bore of the laterally and vertically fixed wash collar with the displacement means;

activating the vacuum means to apply a vacuum to the bore;

activating the probe pumping means to pump wash liquid through the probe and out of the probe tip;

deactivating the probe pumping means;

activating the bore pumping means for pumping wash liquid through the wash collar bore and around the exterior surface of the probe tip;

deactivating the bore pumping means; and deactivating the vacuum means.

4. A method as in claim 3 wherein positioning the probe tip within the wash collar bore is an initial step.

5. A method as in claim 3 wherein the step of deactivating the probe pumping means occurs before the step of activating the bore pumping means.

6. A method as in claim 3 wherein the step of deactivating the probe pumping means occurs after the step of activating the bore pumping means.

7. A method as in claim 3 wherein the steps of activating and deactivating the probe pumping means are timed to create a flow of wash liquid through the probe tip for between about one and two seconds.

8. A method as in claim 3 wherein the steps of activating and deactivating the bore pumping means are timed to create a flow of wash liquid around the exterior surface of the probe tip for less than about one second.

9. A method as in claim 8 wherein the step of deactivating the vacuum means includes deactivating the vacuum means after the bore pumping means has been deactivated for at least one second.

10. A method as in claim 9 wherein the step of deactivating the vacuum means includes deactivating the vacuum means after the bore pumping means has been deactivated for more than one second and less than two seconds.

11. An apparatus as in claim 9 wherein the bore is sized to define a gap between an outside dimension of the probe and an inside dimension of the bore.

12. An apparatus as in claim 11 wherein the wash collar bore includes an upper portion having a first diameter larger than an outside diameter of the probe and a central chamber portion having a diameter larger than the upper portion and including a port in liquid communication with the vacuum means.

13. A method of washing the probe of claim 1 when the probe is displaced vertically downwardly, including the steps of:

positioning the probe tip within the coaxially aligned bore of the laterally and vertically fixed wash collar with the displacement means;

activating the vacuum means to apply a vacuum to the bore;

activating the bore pumping means for pumping wash liquid through the wash collar bore and around the exterior of the probe;

raising the probe until and tip of the probe is disposed within the bore;

activating the probe pumping means to pump wash liquid through the probe and out of the probe tip;

deactivating the probe pumping means;

deactivating the bore pumping means; and deactivating the vacuum means.

14. A method as in claim 13 wherein the step of raising the probe includes raising the probe at about one inch per second.

15. A method as in claim 13 wherein the step of deactivating the bore pumping means includes deactivating the bore pumping means not more than one second after deactivating the probe pumping means.

16. A method as in claim 15 wherein the step of deactivating the vacuum means includes deactivating the vacuum means between one and two seconds after deactivating the bore pumping means.

17. A method as in claim 13 wherein the steps are performed sequentially.

18. An apparatus as in claim 1 wherein the bore pumping means includes pipettor means for aspiring and discharging liquid into and from the probe.

19. A method for using the apparatus of claim 18 including the steps of:

activating the pipettor means to aspirate a liquid into the probe;

retracting the probe such that the probe tip is within the central chamber;

activating the pipettor means to aspirate the liquid into the probe to leave an air slug between the open tip of the probe and aspirated liquid;

activating the vacuum means to apply a vacuum to the bore;

activating the bore pumping means for pumping wash liquid through the wash collar bore and around the exterior of the probe tip;

deactivating the bore pumping means; and deactivating the vacuum means.

* * * * *